United States Patent [19]

Galantay

[11] 4,335,124

[45] Jun. 15, 1982

[54] 1-ALKYL, 1-PHENYL-BUTENES

[75] Inventor: Eugene E. Galantay, Liestal, Switzerland

[73] Assignee: Sandoz, Inc., E. Hanover, N.J.

[21] Appl. No.: 196,474

[22] Filed: Oct. 14, 1980

Related U.S. Application Data

[60] Division of Ser. No. 65,277, Aug. 9, 1979, Pat. No. 4,273,787, which is a continuation of Ser. No. 656,785, Feb. 10, 1976, abandoned, which is a continuation-in-part of Ser. No. 626,943, Oct. 29, 1975, abandoned, which is a continuation-in-part of Ser. No. 390,032, Aug. 20, 1973, abandoned.

[51] Int. Cl.$^3$ .................. A61K 31/03; C07C 25/24; A61K 31/535
[52] U.S. Cl. .................. 424/248.4; 424/353; 424/250; 424/274; 424/267; 424/331; 424/330; 424/248.58; 544/175; 544/106; 544/392; 544/395; 564/442; 570/181; 570/182; 570/185; 568/308; 568/329; 546/246; 546/236; 546/192; 548/565; 548/577
[58] Field of Search .................. 424/248.4, 330, 250, 424/274, 267, 331, 353, 248.58; 544/175, 106, 392, 395; 260/326.5 M, 326.8; 546/240, 192, 236; 564/436, 442; 570/181, 185, 182, 129; 568/308, 329

[56] References Cited

U.S. PATENT DOCUMENTS

| | | | |
|---|---|---|---|
| 2,591,611 | 4/1952 | Ross | 570/182 |
| 2,745,884 | 3/1956 | Kundiger et al. | 424/353 |
| 3,139,377 | 6/1964 | Ratts | 570/185 |
| 3,341,594 | 9/1967 | Thoma et al. | 568/308 |
| 3,373,011 | 3/1968 | Mussell | 570/185 |
| 3,420,853 | 1/1969 | Moed et al. | 568/308 |
| 4,062,978 | 12/1977 | Cole et al. | 568/308 |
| 4,081,474 | 3/1978 | Anderson et al. | 564/442 |
| 4,228,105 | 10/1980 | Jack | 544/175 |

FOREIGN PATENT DOCUMENTS

| | | | |
|---|---|---|---|
| 720845 | 12/1954 | United Kingdom | 570/185 |
| 474526 | 6/1975 | U.S.S.R. | 564/436 |

*Primary Examiner*—Natalie Trousof
*Assistant Examiner*—James H. Reamer
*Attorney, Agent, or Firm*—Gerald D. Sharkin; Richard E. Vila; Frederick H. Weinfeldt

[57] ABSTRACT

The compounds are 4-phenyl-4-lower alkyl-substituted-3-buten-2-ones, and -2-halo-1,3-butadienes, e.g., 2-(p-biphenylyl)-2-penten-4-one, and are useful as pharmaceuticals.

8 Claims, No Drawings

1-ALKYL, 1-PHENYL-BUTENES

This is a division of application Ser. No. 65,277, filed Aug. 9, 1979 now U.S. Pat. No. 4,273,787 which in turn is a continuation, of application Ser. No. 656,785, filed Feb. 10, 1976, now abandoned, which in turn is a continuation-in-part of Ser. No. 626,943, filed Oct. 29, 1975, now abandoned, which in turn is a continuation-in-part of Ser. No. 390,032, filed Aug. 20, 1973, now abandoned.

This invention relates to chemical compounds, and more particularly to 1-alkyl-1-phenyl-substituted-butenes, and to the preparation of such compounds, as well as to pharmaceutical compositions containing such compounds and the use of such compounds.

The compounds of this invention may be conveniently represented by the formula I

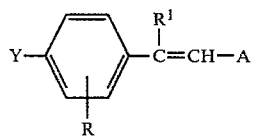

wherein

R is a hydrogen atom or halo having an atomic weight of from about 19 to 80, i.e., fluoro, chloro or bromo;

$R^1$ is lower alkyl, e.g., having from 1 to 3 carbon atoms, such as methyl, ethyl, n-propyl and isopropyl;

Y is halo having an atomic weight of from about 80 to 127, i.e., bromo or iodo, isobutyl, tert.-butyl, cyclohexyl, cyclohexenyl, e.g. cyclohex-1-enyl, or

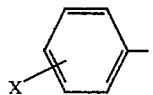

wherein

X is a hydrogen atom, or halo having an atomic weight of from about 19 to 80, i.e., fluoro, chloro or bromo, or lower alkoxy, e.g., having from 1 to 4 carbon atoms, such as methoxy, ethoxy, propoxy, or butoxy, including isomeric forms where such exist; or a radical of the formula

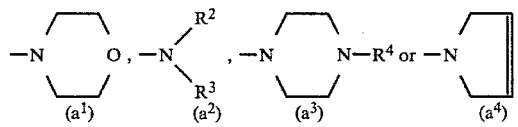

wherein each of $R^2$, $R^3$ and $R^4$, independently, is alkyl having from 1 to 3 carbon atoms, preferably unbranched, or $R^2$ and $R^3$ are joined to form the radical $-(CH_2)_n-$ wherein n is an integer of 4 or 5, i.e. $R^2 + R^3 +$ the nitrogen atom form a pyrrolidino or piperidino ring; or $R^4$ can be H; and A is either of the structures:

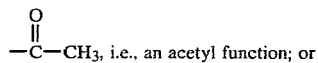

-continued

wherein

Z is halo having an atomic weight of from about 35 to 80, i.e., chloro or bromo; or a pharmaceutically acceptable acid addition salt, thereof.

Thus, Compounds, I comprise two subclasses, depending upon the nature of A; $R^1$, Y, R and Z being as defined above:

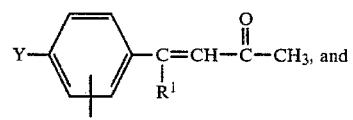

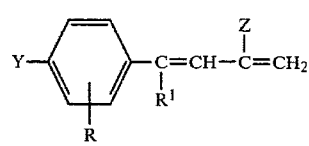

Compounds Ia may be obtained by aqueous acidic treatment (process a) of an appropriate butadienol of the formula II:

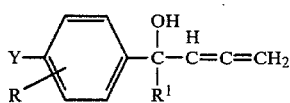

wherein R, Y and $R^1$ are as defined above.

Process (a) involves aqueous acidic treatment of a compound II to obtain the corresponding Compound Ia, and may be carried out employing as the "acidic" source a strong protonating agent, in a suitable medium, at moderate temperatures, e.g., 10° to 100° C., preferably at 15° to 35° C. Where the protonating agent is liquid under the process conditions, it may be used in excess to serve as the medium, however, it is preferable to include a water-miscible solvent such as ethanol or methanol.

Suitable protonating agents include mineral acids, such as hydrochloric or hydrobromic, or sulfuric acid, and aromatic- or (lower) aliphatic sulfonic acids, such as p-toluenesulfonic acid. Process (a) may likewise be carried out using lower carboxylic acids, e.g. having from 1 to 3 carbon atoms, such as acetic acid, but more vigorous reaction conditions may then be necessary.

If hydrochloric or hydrobromic acid is employed as the acidic source in process (a), then in addition to the corresponding Compound Ia product, a corresponding Compound Ib (wherein Z is accordingly either chloro or bromo) will be obtained as a co-product. Thus, by selection of reagents, either Compounds Ia or both classes of Compounds I may be obtained in various proportions. Process (a) may be conveniently represented by Reaction Scheme A, wherein R, $R^1$, Z and Y are as defined above:

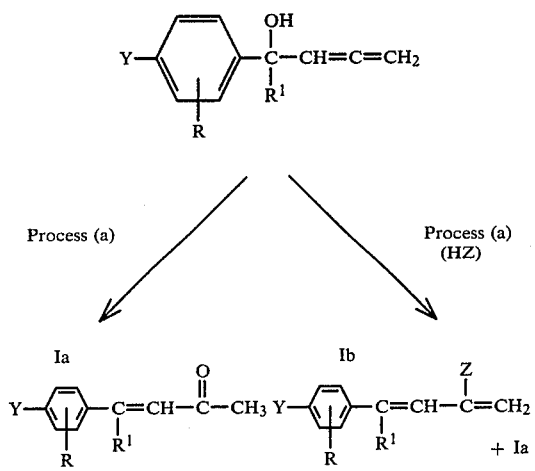

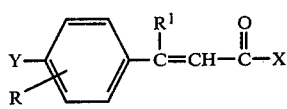

Compounds II, the starting materials of Process (a) are either known compounds or analogs of known compounds are are obtainable by adaption of the methods described in the literature for the preparation of such compounds, e.g., Belgian Pat. No. 792,079.

Compounds Ia may alternatively be prepared by process (b), reacting a compound of formula III:

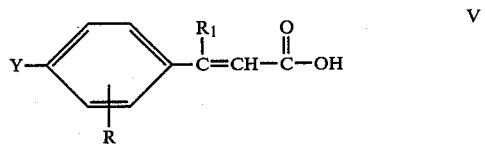

in which Y, R and $R^1$ are as defined and X is chloro or bromo, with a methyl-contributing organometallic reagent IV:

$$CH_3-M, \qquad (IV)$$

in which M is an equivalent of an active metal cation or magnesium bromide or iodide, in an apropotic medium which is not detrimental to the reaction and under anhydrous conditions, and hydrolyzing the resultant adduct.

Process (b) may conveniently be carried out in the conventional manner for carrying out a Grignard-type reaction. The M moiety of the compound IV used may be an alkali metal, e.g. Li, however, the preferred organometallic reagents include Grignard reagents, such as methyl magnesium halides, particularly methyl magnesium bromide. Suitable aprotic media include ethers, such as tetrahydrofuran or diethyl ether, and the reaction is preferably carried out at reduced temperatures of, for example, $-30°$ to $0°$ C. The subsequent hydrolysis may be carried out in conventional manner for hydrolyzing a Grignard-type adduct, for example, with an aqueous salt solution such as saturated ammonium chloride solution. When, in a compound of formula III, Y is an unsubstituted piperazino radical, an additional equivalent of the organometallic reagent is preferably used.

Compounds of formula I may be isolated and purified using conventional techniques. Where required, free base forms of the compounds of formula I in which Y is a radical of formulas $a^1$, $a^2$, $a^3$, or $a^4$, may be converted into acid addition salt forms in conventional manner, and vice versa. Suitable acids for salt formation include mineral acids, such as hydrochloric, hydrobromic, sulphuric and phosphoric acid, and organic acids, such as benzoic, acetic, maleic, p-toluenesulphonic and benzenesulphonic acid.

The compounds of formula I exist as geometric isomers and may be produced in the form of pure cis- or trans-isomers or in the form of isomeric mixtures which may, if desired, be separated, in conventional manner, into individual isomers. The process (a) described above yields the compounds predominantly or substantially in trans-isomeric form but other isomeric forms or mixtures may, if desired, be produced in conventional manner, for example by stereospecific synthesis or by "scrambling" the compounds obtained predominantly or substantially in trans-form as described above, e.g. by UV irradiation, and, if desired, separating the resulting isomeric mixtures using conventional techniques. Process (b), described above, will yield the product in the same geometric form as the starting material. In any event, while the compounds are preferably in pure trans-isomeric form or in the form of isomeric mixtures in which the trans-isomer predominates, e.g. to the extent of 60 to 99%, preferably 70 to 99%, more preferably 80 to 99%, it is to be understood that the invention is not intended to be limited to any particular form of the compounds.

The compounds of formula IV are either known or may be prepared in conventional manner from available materials.

The compounds of formula III may be produced by chlorinating or brominating a corresponding free acid of formula V:

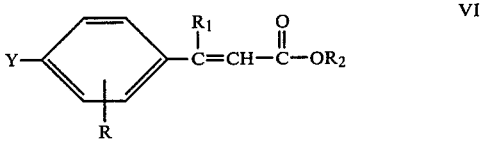

in which R, $R_1$ and Y are as defined above, in conventional manner, for example at a temperature of from $30°$ to $120°$ C. Suitable chlorinating agents include phosphorus trichloride or, preferably, thionyl chloride, and suitable brominating agents include phosphorus tribromide. An inert solvent, e.g. tetrahydrofuran, may suitably be employed. Alternatively, an excess of the chlorinating or brominating agent may, where it is liquid under the reaction conditions, be used to provide a reaction medium.

The resulting compounds of formula III may be isolated and purified using conventional techniques.

The compounds of formula V may be produced by saponifying a compound of formula VI:

$$\text{(VI structure)}$$

in which

R, Y and $R_1$ are as defined above, and $R_2$ is straight chain alkyl of 1 to 6 carbon atoms, preferably ethyl.

The process is suitably effected by heating the compound of formula VI, preferably at a temperature of from $70°$ to $120°$ C., in an aqueous solution of an alkali metal hydroxide, e.g. sodium hydroxide or potassium hydroxide. Preferably, the process is effected in the presence of a water-miscible co-solvent, such as an alkanol of 1 to 4 carbon atoms, e.g. ethanol or methanol.

The resulting compounds of formula V may be isolated and purified using conventional techniques.

The compounds of formula VI are either known or may be produced in conventional manner from available materials.

As indicated above, the compounds of formula I exist in the form of geometric isomers and the geometric form produced by process (b) depends on the configuration of the starting materials of formula III. Thus, for example, the compounds of formula I may be obtained substantially or predominately in trans form by process (b) by using compounds of formula III which are substantially or predominately in trans form. The compounds of formula III may be obtained substantially or predominately in trans form by using, initially, compounds of formula VI which are substantially or predominately in trans form. The compounds of formula VI, substantially or predominately in trans form, may be produced directly by dehydrating a compound of formula VII:

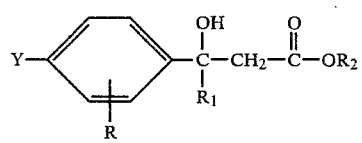

VII in which R, $R_1$, $R_2$ and Y are as defined above.

The process may be carried out by heating a compound of formula VII, suitably at a temperature of from 80° to 200° C., under vacuum, for example 0.01 to 0.5 mm of mercury.

The resulting products may be isolated and purified using conventional techniques.

Other isomeric forms of the compounds of formula VI, which would lead to the corresponding configuration in the final products of formula I, may be produced by conventional methods, for example by stereospecific synthesis from available materials, or by "scrambling" the compounds obtained predominately or substantially in trans form as described above, e.g. by UV irradiation, and, if desired, separating the resulting isomeric mixtures using conventional techniques.

It will be appreciated that particular forms of the compounds of formula I, produced as described above, may themselves be "scrambled" and the resulting isomeric mixtures, if desired, separated by conventional techniques.

The compounds of formula VII are either known or may be produced in conventional manner from available materials. A preferred method for their production involves reaction of a compound of formula VIII:

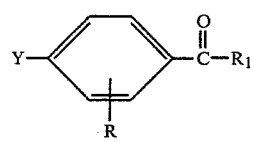

VIII in which R, $R_1$ and Y are as defined above, with a compound of formula IX:

IX in which $R_2$ is as defined above, in an aprotic solvent and under anhydrous conditions, and hydrolysing the resulting adduct.

Suitable solvents include ethers, such as tetrahydrofuran. Suitable reaction temperatures are moderate, for example from 15° to 30° C.

The subsequent hydrolysis may suitably be carried out using water, an aqueous acid base, or an aqueous solution of a salt, e.g., concentrated ammonium hydroxide or dilute sulphuric acid.

The compounds of formula IX may be produced, conveniently in situ, by heating activated zinc, preferably finely divided, e.g., 20 mesh, with $R^2$-bromoacetate in an aprotic solvent, e.g., tetrahydrofuran. The process is, preferably, carried out in the presence of trimethyl borate. The treatment is suitably effected at a temperature of from 15° to 30° C. When trimethyl borate is used in the in situ preparation of a compound IX, it is convenient to include in the hydrolysis step, when using an aqueous base, in addition, glycerine.

The resulting compounds of formula VII may be isolated and purified using conventional techniques.

Compounds VII and IX are either known or may be prepared in conventional manner from available materials, and many are commercially available.

Process (b) and associated processes are conveniently represented by Reaction Scheme B, below, in which R, $R^1$, $R^2$, X, Y and M are as defined above;

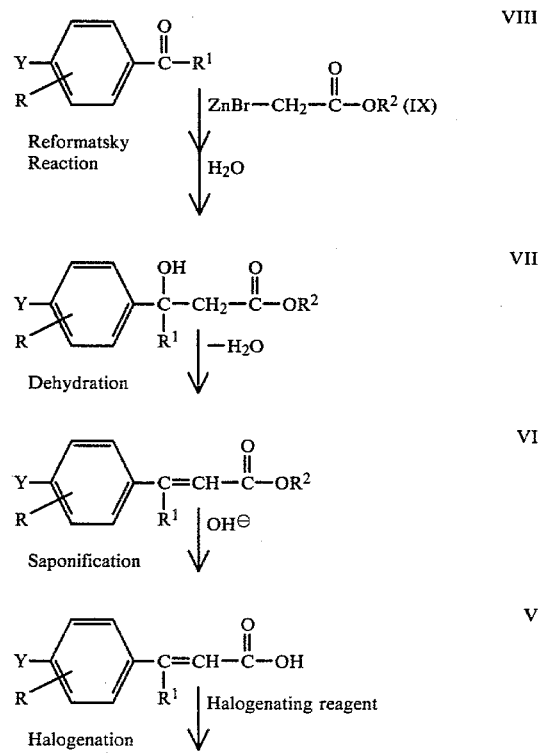

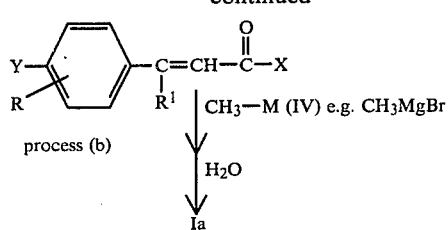

process (b)

STATEMENT OF UTILITY

The compounds of formula I are useful because they possess pharmacological activity in animals. In particular, the compounds I are useful as anti-inflammatory agents as indicated by the Carrageenan induced edema test on rats (oral administration at 5 to 200 mg./kg.). For such use, the compounds may be combined with a pharmaceutically acceptable carrier, and such other conventional adjuvants as may be necessary, and administered orally in such forms as tablets, capsules, elixirs, suspensions and the like or parenterally in the form of an injectable solution or suspension. The dosage administered will, of course, vary depending upon the compounds used and the mode of administration. However, in general, satisfactory results are obtained when administered at a daily dosage of from about 1 milligram to about 200 milligrams per kilogram of body weight, preferably given in divided doses 2 to 4 times a day, or in sustained release form. For most mammals the administration of from about 70 milligrams to about 1500 milligrams of the compound per day provides satisfactory results and dosage forms suitable for internal administration comprise from about 20 milligrams to about 800 milligrams of the compound in admixture with a solid or liquid pharmaceutical carrier or diluent, e.g., a sterile suspension or a solid composition, comprising, for example, from about 5 to 95% of a compound I, e.g., from about 5% to 50% of a compound I.

As noted above, oral administration with carriers may take place in such conventional forms as tablets, dispersible powders, granules, capsules, syrups and elixirs. Such compositions may be prepared according to any method known in the art for manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and absorption in the gastro-intestinal tract and thereby provide a sustained action over a longer period. Similarly, suspensions containing, for example, from about 0.5 to 5% of suspending agent, syrups containing, for example, 10 to 50% of sugar, and elixirs containing, for example from about 20 to 50% of ethenol may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules preferably contain an active ingredient admixed with an inert diluent, e.g., a solid diluent such as calcium carbonate, calcium phosphate and kaolin or a liquid diluent, such as polyethylene glycol or an edible oil, e.g., peanut, corn or sesame oil. The preferred pharmaceutical compositions from the standpoint of preparation and ease of administration are orally administrable compositions, particularly tablets and solid or liquid diluent-filled capsules.

When the substituent Y is a radical of structures $a^1$, $a^2$, $a^3$ or $a^4$ then such compounds I may be similarly administered in the form of their nontoxic pharmaceutically acceptable acid addition salts. Such salts do not materially differ from the free base in their pharmacological effects and are included within the scope of the invention. The acid addition salts are readily prepared by reacting the base with pharmacologically acceptable acids in conventional manner. Representative of such salts are the mineral acid salts such as the hydrochloride, hydrobromide, sulfate, phosphate and the like and the organic acid salts such as the benzoate, acetate, maleate, p-toluenesulfonate, benzenesulfonate and the like.

Representative formulations of a tablet and a capsule prepared by conventional techniques are as follows:

| | Weight | |
|---|---|---|
| Ingredient | Tablet | Capsule |
| 2-(p-biphenylyl)-2-penten-4-one (about 99% trans) | 50 | 50 |
| Tragacanth | 10 | |
| Lactose | 197.5 | 250 |
| Corn Starch | 25 | |
| Talcum | 15 | |
| Magnesium Stearate | 2.5 | |

In the following examples, which illustrate the invention, temperatures are in degrees centigrade, and room temperature is 20° to 30° C., unless indicated otherwise. Olefinic products are understood to be in substantially trans form, unless indicated otherwise. Trans forms are understood to be those in which the olefinic hydrogen atom and $R^1$ are on opposite sides of the double bond.

EXAMPLE 1

2-(p-Biphenylyl)-2-penten-4-one*

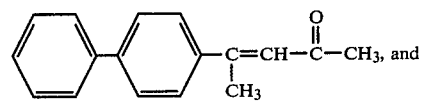

2-(p-biphenylyl)-4-chloro-2,4-pentadiene**

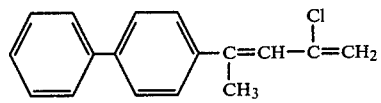

*may also be designated 4-(1,1'-Biphenyl-4-yl)-3-Penten-2-one
**may also be designated 4-(3-Chloro-1-methyl-1,3-butadienyl)-1,1'-biphenyl, or 4-(1,1'-Biphenyl-4-yl)-2-chloro-1,3-pentadiene.

To a solution of 1.5 g. of 2-(p-biphenylyl)-3,4-pentadien-2-ol in 50 ml. of methanol, there is slowly added 2.5 ml. of concentrated hydrochloric acid (12 N). After 3 hours at room temperature, a 10% aqueous solution of sodium acetate is added to the reaction mixture. The precipitate which is formed is filtered and washed with water, and dried over phosphorus pentoxide giving a light yellow solid. The filtrate is then concentrated and more solid is obtained and washed and dried in the same manner. The combined solids are then purified via silica gel preparative plates eluting with methylene chloride. There is obtained two fractions; a first fraction of 2-(p-biphenylyl)-2-penten-4-one, m.p. 130°–133° C., and a second fraction of 2-(p-biphenylyl)-4-chloro-2,4-pentadiene, m.p. 75°–79° C.

EXAMPLE 2

2-(p-Biphenylyl)-2-penten-4-one and
2-(p-biphenylyl)-4-chloro-2,4-pentadiene

To a solution of 10 g. of 2-(p-biphenylyl)-3,4-pentadien-2-ol in 200 ml. of anhydrous methanol is added 3 ml. of concentrated hydrochloric acid. The resulting mixture is stirred at room temperature for 3 hours and then in an ice bath for 2 hours. Solids form and are filtered off and recrystallized from pentane to obtain 2-(p-biphenylyl)-2-penten-4-one.

The filtrate is evaporated to obtain an oil which is purified by placing on a silica gel preparative plate and eluting with methylene chloride to obtain 2-(p-biphenylyl)-4-chloro-2,4-pentadiene, which may also be designated 4-(p-biphenylyl)-2-chloro-1,3-pentadiene.

Repeating the procedure of this example, but using in place of the 2-(p-biphenylyl)-3,4-pentadien-2-ol an equivalent amount of the compound of column (A) there is similarly obtained the compounds of columns (B) and (C):

|   | A | B | C |
|---|---|---|---|
| (a) | 2-(p-tert . butylphenyl)-3,4-pentyldien-2-ol | 2-(p-tert . butylphenyl)-2-penten-4-one | 4-(p-tert . butylphenyl)-2-chloro-1,3-pentadiene. |
| (b) | 2-(p-bromophenyl)-3,4-pentadien-2-ol | 2-(p-bromophenyl)-2-penten-4-one | 4-(p-bromophenyl)-2-chloro-1,3-pentadiene |
| (c) | 2-(p-cyclohexyl-m-chlorophenyl)-3,4-pentadien-2-ol | 2-(p-cyclohexyl-m-chlorophenyl)-2-penten-4-one | 4-(p-cyclohexyl-m-chlorophenyl)-2-chloro-1,3-pentadiene |
| (d) | 2-(p-isobutyl-phenyl)-3,4-pentadien-2-ol | 2-(p-isobutyl-phenyl)-2-penten-4-one | 4-(p-isobutyl-phenyl)-2-chloro-1,3-pentadiene |
| (e) | 2-(p-biphenylyl)-3,4-heptadien-2-ol | 4-(p-biphenylyl)-3-hepten-2-one | 4-(p-biphenylyl)-2-chloro-1,3-heptadiene |
| (f) | 2(p-1'-cyclohexenyl-phenyl)-3,4-pentadien-2-ol | 2(p-1'-cyclohexenyl-phenyl)-2-penten-4-one | 4-(p-1'-cyclohexenyl-phenyl)-2-chloro-1,3-pentadiene |
| (g) | 2-(p-morpholinophenyl)-3,4-pentadien-2-ol | 2-(p-morpholino-phenyl)-2-penten-4-one hydrochloride | 4-(p-morpholinophenyl)-2-chloro-1,3-pentadiene hydrochloride |
| (h) | 2-[p-(N-methyl-piperazinyl)phenyl]-3,4-pentadien-2-ol | 2-[p-(n-methyl-piperazinyl)phenyl]-2-penten-4-one hydrochloride | 4-[p-(N-methyl-piperazinyl)phenyl]-2-chloro-1,3-pentadiene hydrochloride |
| (i) | 2-(p-3-pyrrolinyl-phenyl)-3,4-pentadien-2-ol | 2-(p-3-pyrrolinyl-phenyl)-2-penten-4-one hydrochloride | 4-(p-3-pyrrolinyl-phenyl)-2-chloro-1,3-pentadiene hydrochloride |

EXAMPLE 3

Repeating the procedure of Example 1, but using in place of the concentrated hydrochloric acid used therein, 200 mg. of p-toluenesulphonic acid hydrate in 10 ml. of 90% aqueous ethanol and the reaction mixture kept at room temperature for 18 hours, there is similarly obtained 2-(p-biphenylyl)-2-penten-4-one.

EXAMPLE 4

[Process (a)]

In manner analogous to Example 3, but employing appropriate starting materials in approximately equivalent amounts, the compounds of Examples 2(a) (B), (b) (B), (c) (B), (d) (B), (e) (B) and (f) (B) and the p-toluenesulphonate forms of the compounds of Examples 2(g) (B), 2(h) (B) and 2(i) (B) may be obtained.

EXAMPLE 5

2-(p-Biphenylyl)-2-penten-4-one [process (b)]

(a) 3-(4-Biphenylyl)-2-butenoic acid ethyl ester 6.45 g (0.1 mole) of activated zinc metal (20 mesh) is placed in a flask fitted with a septum inlet and a magnetic stirrer. The system is maintained under a nitrogen atmosphere and kept at a temperature of 25° C. on a water bath. A solution of 19.6 g (0.1 mole) of 4-acetyl-biphenyl in 75 ml of dry tetrahydrofuran and 75 ml of trimethyl borate (distilled from calcium hydride) is injected and the mixture stirred. 11.1 ml (0.1 mole) of freshly distilled ethyl bromoacetate is injected in one shot and the mixture stirred at 25° C. for 12 hours. A mixture of 25 ml of concentrated ammonium hydroxide and 75 ml of glycerine is added, and the aqueous phase is separated and extracted thrice with 25 ml portions of diethyl ether. The combined organic extracts are dried over anhydrous magnesium sulphate and the diethyl ether removed on a rotary evaporator; the residue is vacuum distilled and the fraction distilling at 0.125 mm at 171°–172° C. is collected. Recrystallisation from petroleum ether yields the heading compound.

(b) 3-(4-biphenyl)-2-butenoic acid

The product resulting from (a), above, is mixed with 6 g of 85% potassium hydroxide in 100 ml of aqueous ethanol and the resulting mixture heated on a steam bath for 30 minutes. The mixture is then cooled, poured into ice and extracted thrice with 25 ml portions of diethyl ether. The aqueous phase is filtered over Celite and the filtrate acidified with 2 N hydrochloric acid to pH 4 and cooled. The resulting precipitate is filtered, washed with ether, air dried with suction and then dried under high vacuum at 50° C. to yield the heading compound.

(c) 3-(4-Biphenylyl)-2-butenoic acid chloride

The crude product, resulting from (b), above, is dissolved in 200 ml of dry tetrahydrofuran and 4 ml (0.055 mole) of thionyl chloride is added. The solution is refluxed under a nitrogen atmosphere for 3 hours and the solvent and excess thionyl chloride then distilled off. The resulting residue is flash distilled in a microdistillation apparatus at 145°–153° C. and 0.075 mm to yield the heading compound.

(d) 2-(p-Biphenylyl)-2-penten-4-one 10.0 g (0.039 mole) of the crude acid chloride from (c), above, is dissolved in 200 ml of dry tetrahydrofuran and the solution placed in a 500 ml round bottom flask fitted with a septum inlet and magnetic stirrer, and held under a nitrogen atmosphere. The solution is cooled to −30° C. in a dry ice/isopropanol bath and 19.5 ml (0.039 mole) of a commercial 2 M methyl magnesium bromide solution in dry toluene is added, dropwise, over 30 minutes. After the addition is complete, the mixture is allowed to warm to room temperature and then stirred for 1 hour. The reaction is quenched by the addition of 20 ml of saturated ammonium chloride solution and the organic layer is separated. The aqueous layer is extracted twice with 20 ml portions of ether and the combined organic extracts are then dried over anhydrous magnesium sulphate and evaporated to yield the heading compound, m.p. 130° to 133° C., after recrystallisation from petroleum ether.

EXAMPLE 6

Repeating the procedure of Examples 1 through 3, but using in place of the 2-(p-biphenylyl)-3,4-pentadien-2-ol, an approximately equivalent amount of 3-(p-biphenylyl)-4,5-hexadiene-3-ol, there is similarly obtained 3-(p-biphenylyl)-3-hexene-5-one, mp 63°.

EXAMPLE 7

In manner analogous to Example 5 but employing appropriate starting materials in approximately equivalent amounts, the compounds of Examples 2(a) (B), (b) (B), (c) (B), (d) (B), (e) (B), (f) (B), (g) (B), (h) (B), (i) (B); and of Example 6 may be obtained.

What is claimed is:
1. A compound of the formula

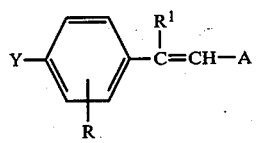

wherein
R is a hydrogen atom or halo having an atomic weight of from about 19 to 80;
$R^1$ is alkyl, having from 1 to 3 carbon atoms;
Y is halo having an atomic weight of from about 80 to 127, isobutyl, tert.-butyl, cyclohexyl, cyclohexenyl, a radical of the formula

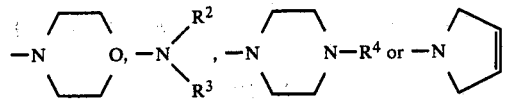

wherein
each of $R^2$ and $R^3$ independently, is alkyl having 1 to 3 carbon atoms, or $R^2$ and $R^3$ are joined to form with the nitrogen atom a pyrrolidino or piperidino ring, and
$R^4$ is a hydrogen atom or alkyl having 1 to 3 carbon atoms; or a radical of the formula

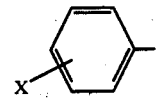

wherein
X is a hydrogen atom, halo having an atomic weight of from about 19 to 80, or alkoxy, having from 1 to 4 carbon atoms; and
A is

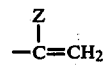

wherein
Z is halo having an atomic weight of from about 35 to 80; or a pharmaceutically acceptable acid addition salt thereof.
2. A compound of claim 1 wherein Z is chloro.
3. A compound of claim 1 wherein $R^1$ is methyl.
4. A compound of claim 2 wherein R is a hydrogen atom and Y is

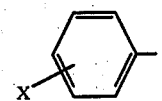

5. The compound of claim 4 wherein X is a hydrogen atom and $R^1$ is methyl.
6. A pharmaceutical composition suitable for use as antiinflammatory comprising a compound of claim 1 and a pharmaceutically acceptable carrier for said compound.
7. A method of treating inflammation in an animal in need of such treatment, comprising internally administering to said animal an amount of a compound of claim 1, effective in reducing said inflammation.
8. A compound of claim 1, in trans form.

* * * * *